(12) United States Patent
Kim

(10) Patent No.: US 10,265,538 B2
(45) Date of Patent: Apr. 23, 2019

(54) COMPOSITE COMPACT-TYPE FAT DECOMPOSITION DEVICE

(71) Applicant: You In Kim, Cheongju-si (KR)

(72) Inventor: You In Kim, Cheongju-si (KR)

(73) Assignee: You In Kim, Cheongju-si, Chungcheongbuk-do (KR)

( * ) Notice: Subject to any disclaimer, the term of this patent is extended or adjusted under 35 U.S.C. 154(b) by 35 days.

(21) Appl. No.: 15/578,394

(22) PCT Filed: Dec. 18, 2015

(86) PCT No.: PCT/KR2015/013971
§ 371 (c)(1),
(2) Date: Nov. 30, 2017

(87) PCT Pub. No.: WO2017/026598
PCT Pub. Date: Feb. 16, 2017

(65) Prior Publication Data
US 2018/0214712 A1     Aug. 2, 2018

(30) Foreign Application Priority Data

Aug. 11, 2015 (KR) .................. 10-2015-0112912

(51) Int. Cl.
*A61B 18/20* (2006.01)
*A61N 5/06* (2006.01)
(Continued)

(52) U.S. Cl.
CPC ............ *A61N 5/0616* (2013.01); *A61B 18/14* (2013.01); *A61B 18/203* (2013.01); *A61N 1/403* (2013.01);
(Continued)

(58) Field of Classification Search
CPC .................. A61B 18/14; A61B 18/203; A61B 2017/00128; A61B 2018/00452;
(Continued)

(56) References Cited

U.S. PATENT DOCUMENTS

| 2008/0114418 A1 | 5/2008 | Myeong et al. |
| 2013/0066300 A1 | 3/2013 | Rhee et al. |
| 2014/0025033 A1 | 1/2014 | Mirkov et al. |

FOREIGN PATENT DOCUMENTS

| JP | 2013-514125 A | 4/2013 |
| JP | 2014-503255 A | 2/2014 |

(Continued)

*Primary Examiner* — Aaron F Roane
(74) *Attorney, Agent, or Firm* — Rabin & Berdo, P.C.

(57) ABSTRACT

The present invention relates to a composite compact-type fat decomposition device, which is characterized in that fat in the epidermis of the skin is decomposed by a beam radiated from LEDs (310), fat in the dermis of the skin is decomposed by a beam radiated from a laser tube (100), and fat in the hypodermis of the skin is decomposed by a high frequency generated by an RF plate. The present invention includes: a handle (200) having a laser tube (100) therein and providing a grip; a rubber tab (230) coupled to a first end of the handle and protecting a power line; a ring-shaped LED PCB (300) coupled to a second end of the handle and equipped with LEDs (310); an RF plate support (400) having the LED PCB (300) on a first side and an RF plate (410) on a second side; the RF plate (410) decomposing fat by generating a high frequency; and a controller (500) controlling operations of the LEDs (310), the laser tube (100), and the RF plate (410), in which a beam radiated from the LEDs (310) decomposes fat in the epidermis of the skin, a beam radiated from the laser tube decomposes fat in the dermis of the skin, and the high frequency generated by the RF plate (410) decomposes fat in the hypodermis of the skin.

7 Claims, 5 Drawing Sheets

(51) Int. Cl.
*A61N 1/40* (2006.01)
*A61B 18/14* (2006.01)
*A61B 18/00* (2006.01)
*A61N 5/067* (2006.01)
*A61B 17/00* (2006.01)
*A61B 18/18* (2006.01)

(52) U.S. Cl.
CPC ............... *A61B 2017/00128* (2013.01); *A61B 2018/00452* (2013.01); *A61B 2018/00464* (2013.01); *A61B 2018/00642* (2013.01); *A61B 2018/00678* (2013.01); *A61B 2018/00708* (2013.01); *A61B 2018/00791* (2013.01); *A61B 2018/00797* (2013.01); *A61B 2018/00898* (2013.01); *A61B 2018/00994* (2013.01); *A61B 2018/1807* (2013.01); *A61B 2018/207* (2013.01); *A61N 2005/067* (2013.01); *A61N 2005/0629* (2013.01); *A61N 2005/0644* (2013.01); *A61N 2005/0652* (2013.01); *A61N 2005/0659* (2013.01); *A61N 2005/0663* (2013.01)

(58) Field of Classification Search
CPC A61B 2018/00464; A61B 2018/00642; A61B 2018/00678; A61B 2018/0708; A61B 2018/00791; A61B 2018/00797; A61B 2018/00898; A61B 2018/00994; A61B 2018/1807; A61B 2018/207; A61N 1/403; A61N 5/0616; A61N 2005/0629; A61N 2005/0644; A61N 2005/0652; A61N 2005/0659; A61N 2005/0663; A61N 2005/067
USPC .......................................................... 607/89
See application file for complete search history.

(56) References Cited

FOREIGN PATENT DOCUMENTS

| | | |
|---|---|---|
| KR | 10-0653441 B1 | 12/2006 |
| KR | 10-1406204 B1 | 6/2014 |
| KR | 10-2014-0141489 A | 12/2014 | ured at a middle portion in a longitudinal direction to stably
COMPOSITE COMPACT-TYPE FAT DECOMPOSITION DEVICE

TECHNICAL FIELD

The present invention relates to a composite compact-type fat decomposition device and, more particularly, a composite compact-type fat decomposition device that decomposes fat in the entire skin tissue including the epidermis, the dermis, and the hypodermis with one device by integrating an LED, a laser tube, and an RF plate.

BACKGROUND ART

With the improvement of life quality, people are more interested in health and appearances than at any other time. One area of concern in terms of not only health, but also appearances or shape is fat.

The reason for body fat accumulation has been analyzed as being basically caused by more caloric intake from food than the calories consumed by metabolism and exercise. Accordingly, the conventional method of removing body fat is to promote fat metabolism by refraining from excessive intake of food and performing sufficient aerobic exercise. However, dieting and exercise require constant practice and dedication, so it is difficult to obtain satisfactory results.

Meanwhile, suction lipectomy has been introduced as a surgical method for fat removal, so it is possible to physically remove fat of desired parts. However, this surgical method removes fat tissues, but may injure the nervous system, blood vessels, and muscles around the fat tissues and there is a burden of general anesthesia, and if severe, it causes death due to a medical accident related to anesthesia. Accordingly, safer, non-invasive, and non-surgical methods have been proposed.

Recently, an optical method has become attractive as a non-invasive method for fat decomposition. This method promotes fat decomposition by radiating light having specific wavelengths to the skin. According to academia, it has been reported that the absorption rate of fat is the highest at a specific wavelength.

In general, an optical fat decomposition device is operated in the principle of promoting fat decomposition by radiating light having a specific wavelength to the skin.

However, since the penetration depth of light into a skin tissue depends on the magnitudes of wavelength, there is a need for separate devices for each layer of the skin in order to decompose fat in all skin layers including the epidermis, the dermis, and the hypodermis. Patients who desire such a fat decomposition procedure necessarily feel a burden in terms of the process of the procedure, money, and time because several devices are needed.

Accordingly, it is required to develop a compact fat decomposition device that can decompose fat in all skin layers including the epidermis, the dermis, and the hypodermis.

DISCLOSURE

Technical Problem

The present invention has been made in an effort to solve the problems and an object of the present invention is to provide a composite compact-type fat decomposition device that decomposes fat in all skin layers including the epidermis, the dermis, and the hypodermis, using three instruments integrated in one device.

Another object of the present invention is to provide a mode selector for selectively operating one of more instruments, depending on the state of the use's skin.

Another object of the present invention is to provide a mode-alternating controller that increases fat decomposition efficiency by alternately applying a stimulus in the depth direction of the skin tissue.

Another object of the present invention is to stop operation of a fat decomposition device when temperature sensors sense a temperature equal to or higher than critical temperature set in advance.

Another object of the present invention is to provide an LED-alternating controller that increases fat decomposition efficiency by alternately applying a stimulus in the circumferential direction of an LED PCB by alternately operating LEDs.

Another object of the present invention is to prevent a rubber tap from twisting by forming spiral grooves on the rubber tap surrounding a power line.

Technical Solution

The present invention includes: a handle having a laser tube therein and providing a grip; a rubber tab coupled to a first end of the handle and protecting a power line; a ring-shaped LED PCB coupled to a second end of the handle and equipped with LEDs; an RF plate support having the LED PCB on a first side and an RF plate on a second side; the RF plate decomposing fat by generating a high frequency; and a controller controlling operations of the LEDs, the laser tube, and the RF plate, in which a beam radiated from the LEDs decomposes fat in the epidermis of the skin, a beam radiated from the laser tube decomposes fat in the dermis of the skin and the high frequency generated by the RF plate decomposes fat in the hypodermis of the skin.

The controller may include a mode selector selectively operating one or more of the LEDs, the laser tube, and the RF plate, depending on states of a user's skin.

The controller may include a mode-alternating controller increasing the fat decomposition efficiency by alternately operating instruments selected by the mode selector to alternately apply a stimulus in a depth direction of a skin tissue.

The device may further include a plurality of temperature sensors disposed on the LED PCB or the RF plate, in which when the temperature sensors sense a temperature equal to or higher than critical temperature set in advance, the device may stop operating.

The device may further include an LED-alternating controller increasing the fat decomposition efficiency by alternately applying a stimulus in a circumferential direction of the LED PCB by alternately operating the LEDs on the LED PCB.

The handle may have a convex portion radially protruding at a middle portion in a longitudinal direction to stably support the handle when held in a palm.

The handle may be made of urethane having a high friction coefficient to prevent breakage due to dropping.

Grooves may be formed on an outer side of the rubber tap to remove heat generated by any one of the LEDs (310), the laser tube (100), and the RF plate.

The grooves on the rubber tab may be spirally formed to prevent twist of the rubber tap.

A beam radiated from the LEDs may have a wavelength of 660 nm and a beam radiated from the laser tube 100 may have a wavelength of 980 nm.

Advantageous Effects

According to the present invention, since the LEDs, laser tube, and RF plate are integrated in one device, it is possible to decompose fat in all skin layers including the epidermis, the dermis, and the hypodermis.

Further, since the mode selector is provided, it is possible to selectively operate one or more instruments, depending on the state of user's skin.

Further, since the mode-alternating controller is provided, it is possible to increase fat decomposition efficiency by alternately applying a stimulus in the depth direction of a skin tissue.

Further, since the temperature sensors are provided, it is possible to stop operation of the device when the temperature sensors sense a temperature equal to or higher than critical temperature set in advance.

Further, since the LED-alternating controller is provided, it is possible to increase fat decomposition efficiency by alternately applying a stimulus in the circumferential direction of LED PCB.

Further, since spiral grooves are formed on the rubber tap surrounding the power line, it is possible to prevent twisting of the rubber tap.

BEST MODE

The present invention includes: a handle having a laser tube (100) therein and providing a grip; a rubber tab coupled to a first end of the handle and protecting a power line; a ring-shaped LED PCB coupled to a second end of the handle and equipped with LEDs; an RF plate support having the LED PCB on a first side and an RF plate on a second side; the RF plate decomposing fat by generating a high frequency; and a controller controlling operations of the LEDs, the laser tube, and the RF plate.

MODE FOR INVENTION

Hereinafter, preferred embodiments of the present invention will be described in detail with reference to the accompanying drawings.

The present invention is not limited to the following embodiments, but may be implemented in various ways and the embodiments are provided to make the present invention clear and help those skilled in the art completely understand the present invention.

The operation principle of an optical fat decomposition device is to promote fat decomposition by radiating light having specific wavelengths to the skin. The penetration depth of light into the skin tissue depends on the magnitudes of wavelength.

A skin tissue is composed of the epidermis, the dermis, and the hypodermis. Since the penetration depths are different, separate instruments are required for the skin layers to decompose fat in the entire skin tissue composed of the epidermis, the dermis, and the hypodermis.

Figure 1:
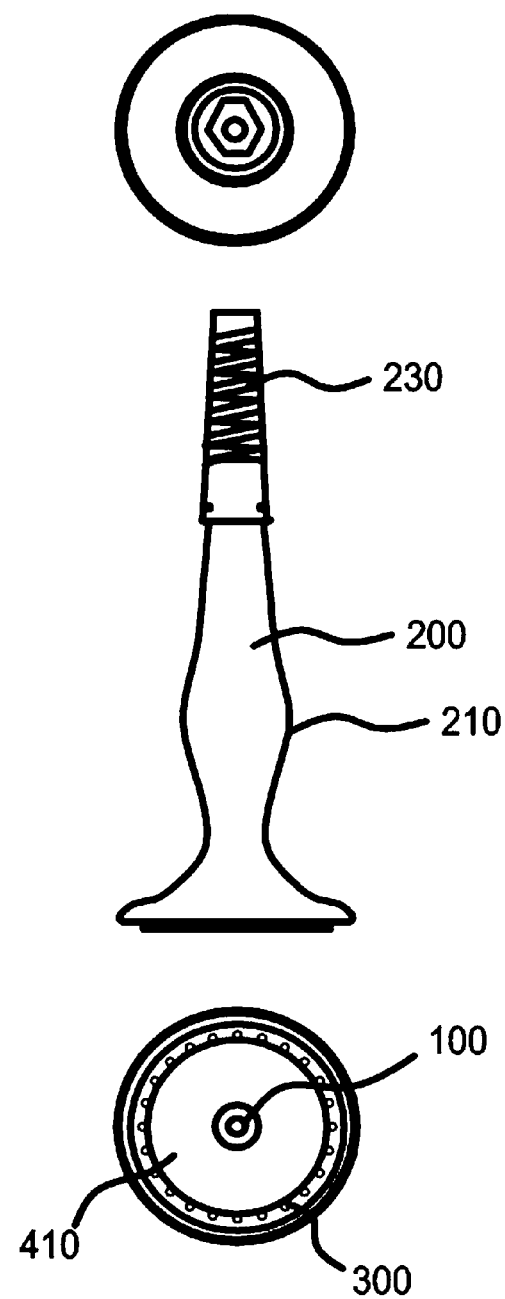
FIG. 1 is an assembly view of a composite fat decomposition device according to the present invention.
Figure 2:
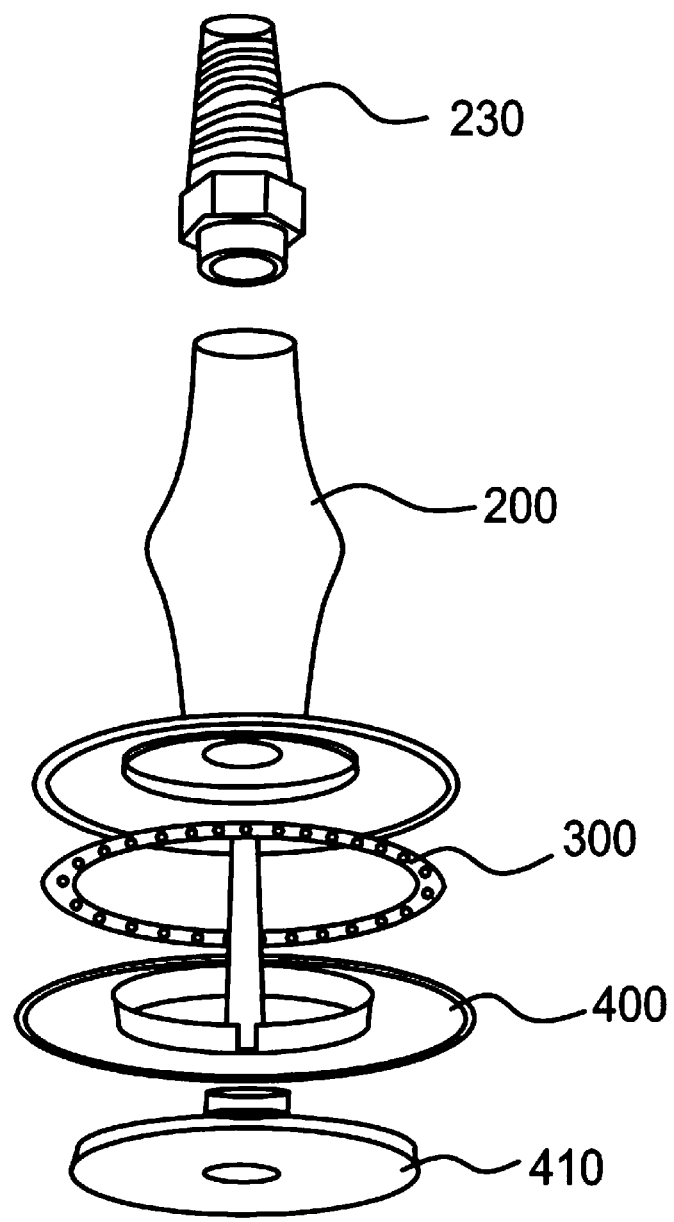
FIG. 2 is an exploded perspective view of the composite fat decomposition device according to the present invention.
Figure 3:
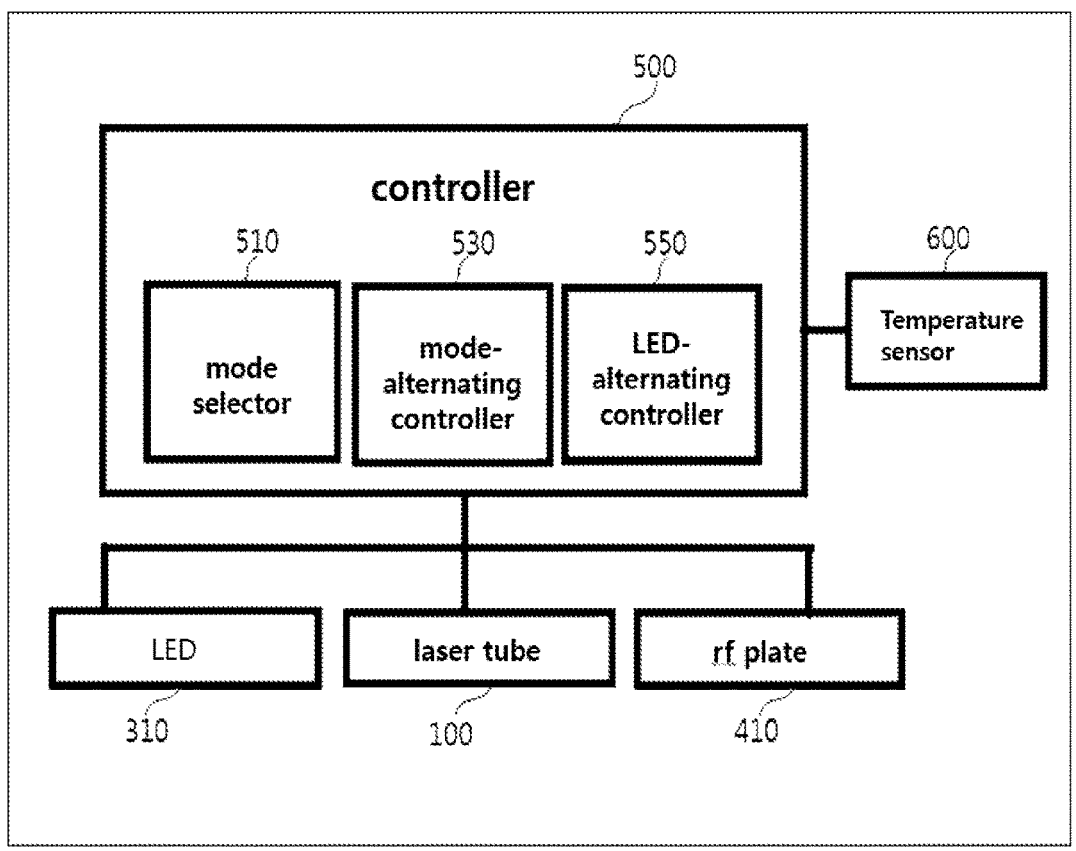
FIG. 3 is a block diagram of the composite fat decomposition device according to the present invention.

FIG. 1 is an assembly view of a composite compact-type fat decomposition device according to the present invention and FIG. 2 is an exploded perspective view of the composite compact-type fat decomposition device according to the present invention. As show in FIGS. 1 and 2, the composite fat decomposition device according to the present invention includes a laser tube 100, a handle 200, a rubber tap 230, an LED PCB 300 having LEDs, an RF plate support 400, an RF plate 410, and a controller 500.

The laser tube 100 according to the present invention radiates a laser beam having a wavelength of 980 nm through a tube at the center. The laser beam having a wavelength of 980 nm is usually absorbed in a dermis and decomposes fat therein.

A laser providing a wavelength of 660 nm has a relatively high cost to be manufactured, so a plurality of LEDs 310 arranged around the edge of the LED PCB 300 is employed as light sources. Accordingly, LEDs of which the wavelength is 660 nm are used in the present invention. An LED beam having a wavelength of 660 nm is usually absorbed in an epidermis and decomposes fat therein.

The RF plate 410 is disposed inside the LED PCB 300 to decompose fat accumulated in a deep layer. When an RF high frequency is applied to the RF plate 410, polarization in which positive (+) ions and negative (−) ions of cellular molecules in the skin tissue are respectively attracted to a cathode and an anode is generated, and Joule heat is generated in the skin tissue. The Joule heat decomposes fat in the hypodermis of the skin tissue.

When a patient desires a fat decomposition procedure, it is required to check parts to be operated by imaging his/her skin tissues. An operator checks parts of the patient's skin tissues with excessively accumulated fat and then performs the fat decomposition procedure on the corresponding skin tissues.

As the result of imaging, when the epidermis and the dermis need fat decomposition or when the epidermis and the deep layer need fat decomposition, it is very troublesome and requires much cost and time to use separate devices for the skin tissues. However, the composite fat decomposition device according to the present invention decomposes fat in the entire skin tissue including the epidermis, the dermis, and the hypodermis using the LEDs 310, laser tube 100, and RF plate 410.

The laser tube 100 that radiates a laser is disposed in the handle 200 that provides a grip.

The rubber tap 230 is disposed at a first end of the handle to protect a power line and prevent twisting of the power line.

The ring-shaped LED PCB 300 equipped with the LEDs 310 is coupled to a second end of the handle. The LED PCB 300 is coupled to a first side of the RF plate support 400 and the RF Plate 410 is coupled to a second end of the LED PCB. As described above, according to the composite compact-type fat decomposition device of the present invention, three instruments are assembled in a compact size in one device, so the device can perform a procedure on all skin layers including the epidermis, the dermis, and the hypodermis.

The controller 500 according to the present invention controls the operations of the LEDs 310, laser tube 100, and RF plate 410. The controller 500 includes a mode selector 510, so it selectively operates any one or more of the LEDs 310, laser tube 100, and RF plate 410, depending on the states of the user's skin. For example, only the LEDs 310 can be operated in order to decompose fat only in the epidermis, and when the dermis and the hypodermis need fat decomposition, the laser tube 100 and the RF plate 410 both can be operated.

The efficiency of fat decomposition is increased when a change is given to an area that is stimulated rather than when only one portion of a tissue is continuously treated. Accordingly, the controller 500 according to the present invention includes a mode-alternating controller 530. The mode-alternating controller 530 alternately operates the instruments selected by the mode selector 510 to alternately apply a stimulus in the depth direction of a skin tissue, thereby increasing the fat decomposition efficiency.

The LEDs 310 are mounted on the ring-shaped LED PCB 300. The controller 500 according to the present invention includes an LED-alternating controller 550. The LED-alternating controller 550 increases the fat decomposition efficiency by alternately applying a stimulus in the circumferential direction of the LED PCB 300 by alternately operating the LEDs 310. Since the mode-alternating controller 530 and the LED-alternating controller 550 are provided, a stimulus is applied simultaneously in the depth direction of a skin tissue and the circumferential direction of the LED PCB 300, so the fat decomposition efficiency can be increased through more various stimuli.

Figure 4:
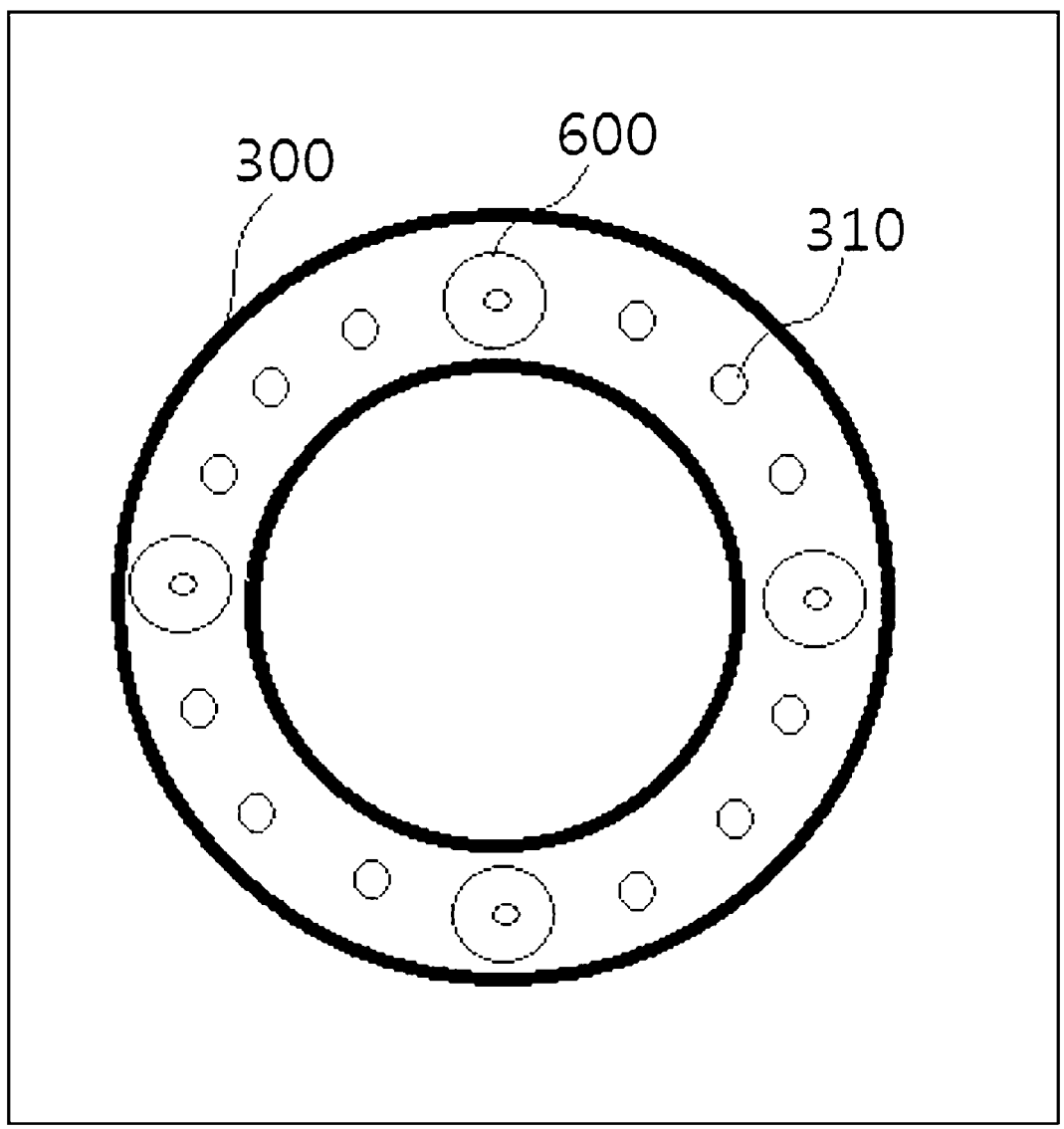
FIG. 4 is a plan view of an LED PCB according to the present invention.
Figure 5:
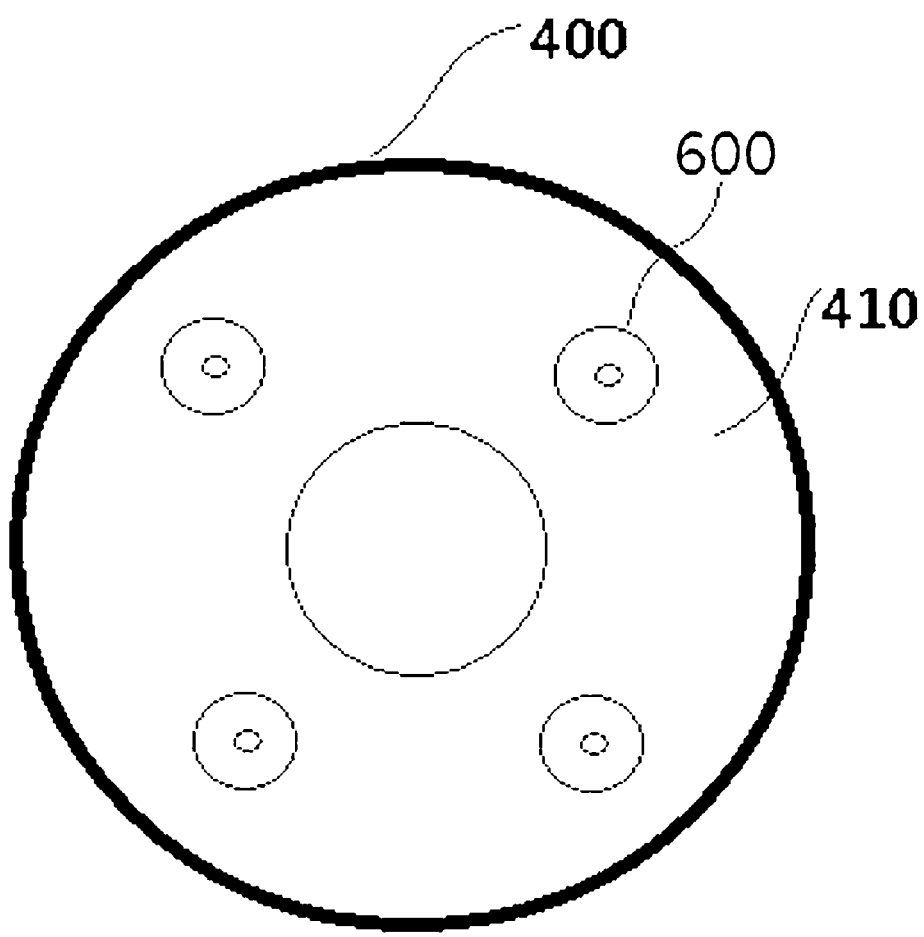
FIG. 5 is a plan view of an RF plate according to the present invention.

FIG. 4 is a plan view of the LED PCB 300 according to the present invention and FIG. 5 is a plan view of the RF plate 410 according to the present invention. As shown in FIG. 4, temperature sensors 600 are disposed on the LED PCB 300. Four temperature sensors 600 are arranged with gaps of 90 degrees, but if necessary, the number of the temperature sensors 600 may be increased or decreased.

Temperature sensors 600 are also disposed on the RF plate 410. Four temperature sensors 600 are arranged with gaps of 90 degrees, but they are deviated at 45 degrees from the temperature sensors 600 on the LED PCB 300. This is for evenly measuring a temperature of the skin tissue in all directions.

The temperature sensors 600 are provided to prevent a skin tissue from being overheated and burned by energy that is applied to the skin tissue in a fat decomposition procedure. When the temperature sensors 600 on the LED PCB 300 or the RF plate 410 sense a temperature equal to or higher than a critical temperature set in advance, the controller 500 stops the procedure of the fat decomposition device on the basis of the sensed temperature. Further, it is also preferable to warn an operator by installing an alarm etc. in the controller 500.

The handle 200 has a convex portion radially protruding at the middle portion in the longitudinal direction. The convex portion 210 acts like a step that is locked to the palm when an operator drops it, thereby preventing damage to the LEDs 310 or the laser tube 100 that is vulnerable to shock. The handle 200 is made of a material having a high friction coefficient to prevent breakage due to dropping. Urethane is preferable for the material of the handle 200.

The rubber tap 230 that protects the power line is coupled to the first end of the handle. Grooves are formed on the outer side of the rubber tap 230 so that air can freely flow. Heat generated by any one of the LEDs 310, laser tube 100, and RF plate 410 is quickly removed through heat exchange with the surrounding air by the grooves.

The grooves of the rubber tap 230 are spirally formed. The spiral grooves generate resistance against torsion of the rubber tap 230. Accordingly, the rubber tap 230 having the power line is not twisted.

Although the present invention was described above with reference to the exemplary drawings, the present invention is not limited by the embodiments and drawings and may be modified in various ways by those skilled in the art with departing from the scope of the present invention. Further, even though the effects by the configuration of the present invention were not clearly described in the description of the embodiments of the present invention, expectable effects from the configuration should be admitted.

What is claimed is:

1. A composite compact-type fat decomposition device, comprising:
    a laser tube (100) radiating a laser;
    a handle (200) having the laser tube (100) therein and providing a grip;
    a rubber tab (230) coupled to a first end of the handle and protecting a power line;
    a ring-shaped LED PCB (300) coupled to a second end of the handle and equipped with LEDs (310);
    an RF plate support (400) having the LED PCB (300) on a first side and an RF plate (410) on a second side;
    the RF plate (410) seated on the RF plate support (400) and decomposing fat by generating a high frequency; and
    a controller (500) controlling operations of the LEDs (310), the laser tube (100), and the RF plate (410), wherein a beam radiated from the laser tube (100) decomposes fat in a dermis of skin and the high frequency generated by the RF plate 410 decomposes fat in a hypodermis of the skin.

2. The device of claim 1, wherein the controller (500) includes:
    a mode selector (510) selectively operating one or more of the LEDs (310), the laser tube (100), and the RF plate (410), depending on states of a user's skin; and
    a mode-alternating controller (530) increasing the fat decomposition efficiency by alternately operating instruments selected by the mode selector (510) to alternately apply a stimulus in a depth direction of a skin tissue.

3. The device of claim 1, further comprising a plurality of temperature sensors (600) disposed on the LED PCB (300) or the RF plate (410), wherein when the temperature sensors (600) sense temperature equal to or higher than critical temperature set in advance, the device stops operating.

4. The device of claim 1, further comprising an LED-alternating controller (550) increasing the fat decomposition efficiency by alternately applying a stimulus in a circumferential direction of the LED PCB (300) by alternately operating the LEDs (310) on the LED PCB (300).

5. The device of claim 1, wherein the handle (200) has a convex portion radially protruding at a middle portion in a longitudinal direction to stably support the handle (200) when held in a palm, and is made of urethane having a high friction coefficient to prevent breakage due to dropping.

6. The device of claim 1, wherein grooves are spirally formed on an outer side of the rubber tap (230) to prevent twist thereof and to remove heat generated by any one of the LEDs (310), the laser tube (100), and the RF plate (410).

7. The device of claim 1, wherein a beam radiated from the LEDs (310) has a wavelength of 660 nm and a beam radiated from the laser tube (100) has a wavelength of 980 nm.

* * * * *